United States Patent [19]

Gray et al.

[11] Patent Number: 5,740,803
[45] Date of Patent: Apr. 21, 1998

[54] LOCATING THE CENTER OF THE ENTRANCE PUPIL OF AN EYE AFTER PUPIL DILATION

[75] Inventors: Gary P. Gray; Charline A. Gauthier, both of Orlando, Fla.; Ioannis G. Pallikaris, Crete, Greece

[73] Assignee: Autonomous Technologies Corporation, Orlando, Fla.

[21] Appl. No.: 813,079

[22] Filed: Mar. 7, 1997

[51] Int. Cl.[6] ............................................. A61B 3/107
[52] U.S. Cl. ....................... 128/653.1; 128/664; 128/745; 351/211; 351/212
[58] Field of Search ............................... 128/664, 665, 128/653.1, 745; 351/211, 212, 221, 205

[56] References Cited

U.S. PATENT DOCUMENTS

| | | | |
|---|---|---|---|
| 4,019,813 | 4/1977 | Cornsweet et al. | 351/14 |
| 4,721,378 | 1/1988 | Volk | 351/205 |
| 4,761,071 | 8/1988 | Baron | 351/212 |
| 5,506,634 | 4/1996 | Wei et al. | 351/221 |
| 5,512,966 | 4/1996 | Snook | 351/205 |
| 5,526,073 | 6/1996 | Mattioli | 351/212 |
| 5,640,962 | 6/1997 | Jean et al. | 128/664 |

*Primary Examiner*—Marvin M. Lateef
*Assistant Examiner*—Eleni Mantis Mercader

[57] ABSTRACT

A method and system are provided for locating the center of the entrance pupil of an eye after the pupil thereof has been dilated. A first image of an eye is formed prior to pupil dilation. The center of the undilated pupil is referenced to a reference image of an anatomical landmark of the eye that appears in the first image. A second image of the eye is then formed when the pupil is dilated. When the reference image is positioned on an image of the anatomical landmark appearing in the second image, the center of the undilated pupil referenced to the reference image defines the center of the entrance pupil of the eye.

13 Claims, 3 Drawing Sheets

LOCATING THE CENTER OF THE ENTRANCE PUPIL OF AN EYE AFTER PUPIL DILATION

FIELD OF THE INVENTION

The invention relates generally to ophthalmic procedures, and more particularly to a method and system for locating the center of the entrance pupil of an eye after the pupil thereof has been dilated.

BACKGROUND OF THE INVENTION

A variety of ophthalmic treatment procedures involving the reshaping or removing (i.e., ablation) of corneal material are being used and/or evaluated by the medical profession. For example, one type of corneal ablation surgery uses a small laser beam focused at various locations on the cornea in accordance with a prescribed ablation pattern. The ablation pattern, designed to alter the optical power of the cornea by removal of corneal material, must be accurately centered on the cornea. Optically, the radius of curvature of the front surface of the cornea is altered by the ablative surgery. The intent of the procedure is to alter the radius of curvature without changing the optical axis of the eye's cornea-lens optical system and without introducing astigmatic effects.

During many ophthalmic treatment procedures, the eye's pupil may be dilated for a variety of reasons. For example, in a corneal ablation procedure using the system described in U.S. patent application Ser. No. 08/232,615, filed Apr. 25, 1994, owned by the same assignee as the present invention, the pupil is dilated to facilitate operation of the eye tracking portion of the apparatus. However, the pupil does not typically dilate symmetrically. Thus, the center of the dilated pupil generally appears shifted with respect to the center of the undilated or natural pupil. Since the true optical axis of the eye's cornea-lens optical system corresponds closely with the center of the natural pupil, it is highly desirable to orient the ablation laser relative to this reference point when the eye's pupil is dilated. The same is true for any procedure requiring pupil dilation and optical centration.

SUMMARY OF THE INVENTION

Accordingly, it is an object of the present invention to provide a method and system for determining the optical axis or center of an eye's cornea-lens optical system when the eye's pupil is dilated.

Another object of the present invention is to provide a method and system for locating the optical center of an eye's cornea-lens optical system during an ophthalmic treatment procedure in which the eye's pupil is dilated.

Other objects and advantages of the present invention will become more obvious hereinafter in the specification and drawings.

In accordance with the present invention, a method and system are provided for locating the center of the entrance pupil of an eye after the undilated pupil thereof is no longer available, e.g., the pupil has been dilated. A first image of an eye is formed with its pupil in an undilated state. The center of the undilated pupil is referenced to a reference image of an anatomical landmark of the eye that appears in the first image. Image coordinates are used to define the center of the undilated pupil and the reference image. A second, potentially "live" image of the eye is then formed when the pupil is dilated. The reference image is positioned on an image of the anatomical landmark appearing in the second image. The center of the undilated pupil referenced to the reference image defines the optical center of the eye when the pupil is dilated. In one embodiment, the anatomical landmark is the eye's limbus which is unaffected by pupil dilation.

DETAILED DESCRIPTION OF THE INVENTION

Figure 1:
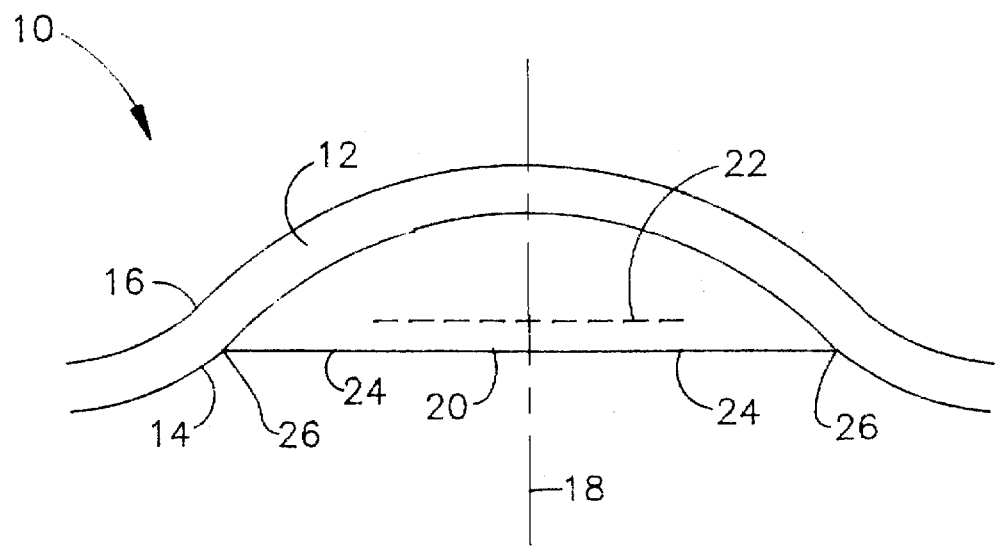
FIG. 1 is a schematic side view of an eye referencing the critical elements thereof in terms of understanding the present invention.

Referring now to the drawings, and more particularly to FIG. 1, a schematic side view of a portion of an eye is shown and referenced generally by numeral 10. The elements of eye 10 necessary for understanding the present invention will be described briefly below. The cornea 12 of eye 10 is assumed to be characterized by an interior surface 14 and an exterior surface 16 that are concentric with one another. A line referenced by numeral 18 normal to an undilated or natural pupil 20 and passing through the centers of curvature of surfaces 14 and 16 is the optical axis of cornea 12. It is optical axis 18 that is the desired reference center of ablation of corneal (laser) ablation surgery. However, it is to be understood that the method and system described herein can be used for other ophthalmic procedures where the location of the optical axis or center of the eye must be known when the undilated pupil is no longer available, e.g., after pupil dilation. The remaining portions of eye 10 depicted in FIG. 1 are the iris 24 extending outward from natural pupil 20 to interior surface 14 of cornea 12. The circle of intersection between iris 24 and interior surface 14 is an anatomical landmark known as the limbus, the position thereof being indicated by reference numeral 26.

According to published data by Uozato et al. in "Centering Corneal Surgical Procedures," American Journal of Ophthalmology, March 1987, p. 264, optical axis 18 is coincident with the center of the entrance pupil of the eye which is the virtual image of natural pupil 20 formed by cornea 12. Thus, the entrance pupil, referenced by dashed line 22, is what will be seen from a point on optical axis 18 beyond exterior surface 16. Entrance pupil 22 appears at a position that is 3.05 millimeters from interior surface 14 (measured along optical axis 18) or 0.55 millimeters closer to interior surface 14 than natural pupil 20. Additionally, entrance pupil 22 is approximately 14% larger than natural pupil 20.

Figure 2:
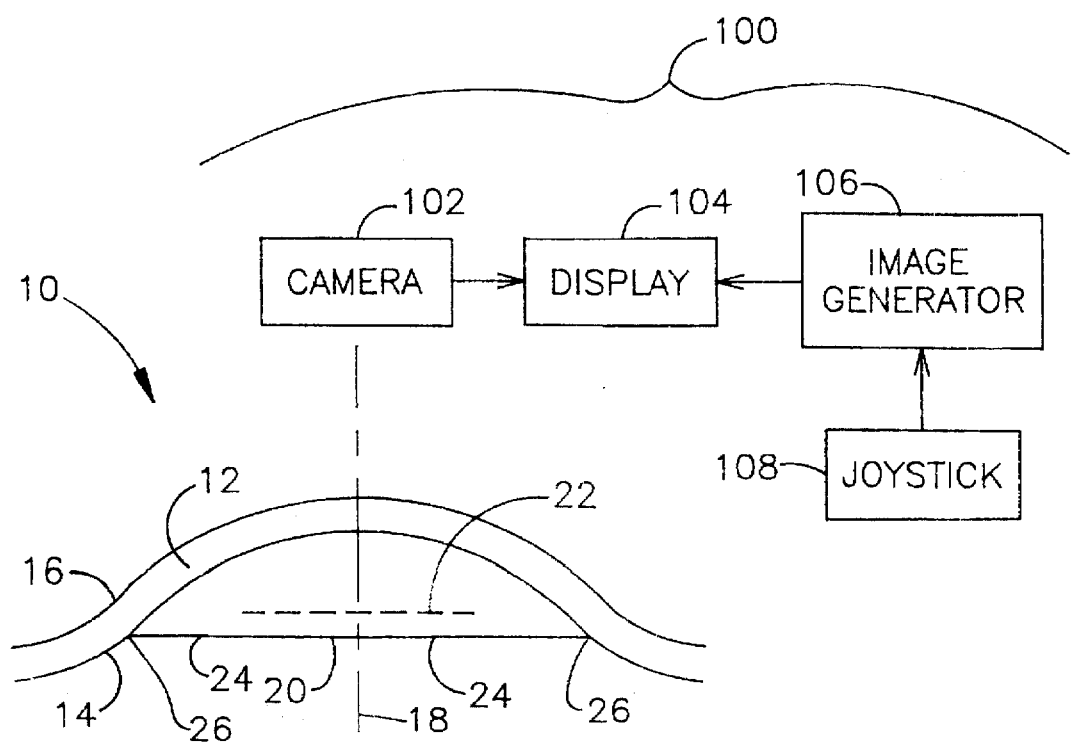
FIG. 2 is a functional block diagram of the system used to carry out the method of the present invention.

In FIG. 2, a block diagram of a system for carrying out the method of the present invention is shown and referenced generally by numeral 100. In the illustrated embodiment, system 100 includes a camera 102 positioned to image eye 10 along optical axis 18. Camera 102 provides video image data of eye 10 to a display 104. Coupled to display 104 is an image generator 106 (e.g., a personal computer programmed with commercially-available computer aided design software) capable of generating and overlaying geometric images onto the image (of eye 10) appearing on display 104. A joystick (or mouse) 108 is coupled to image generator 106 and is used to provide operator inputs to image generator 106 in order to control the size and position of the geometric images overlaid on the image (of eye 10) on display 104.

Figure 3:
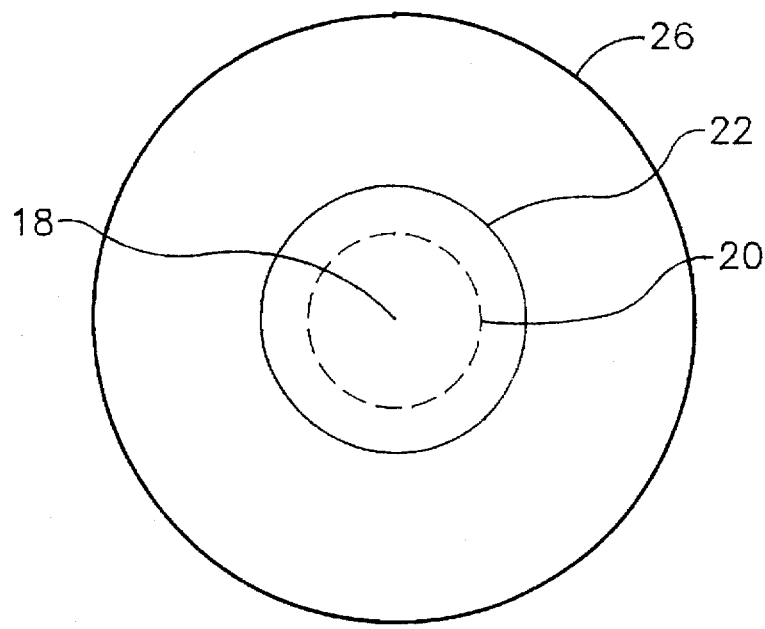
FIG. 3 is a schematic view of an eye's image for showing the position of the overlaid images used in the present invention when the eye's pupil is not dilated.
Figure 4:
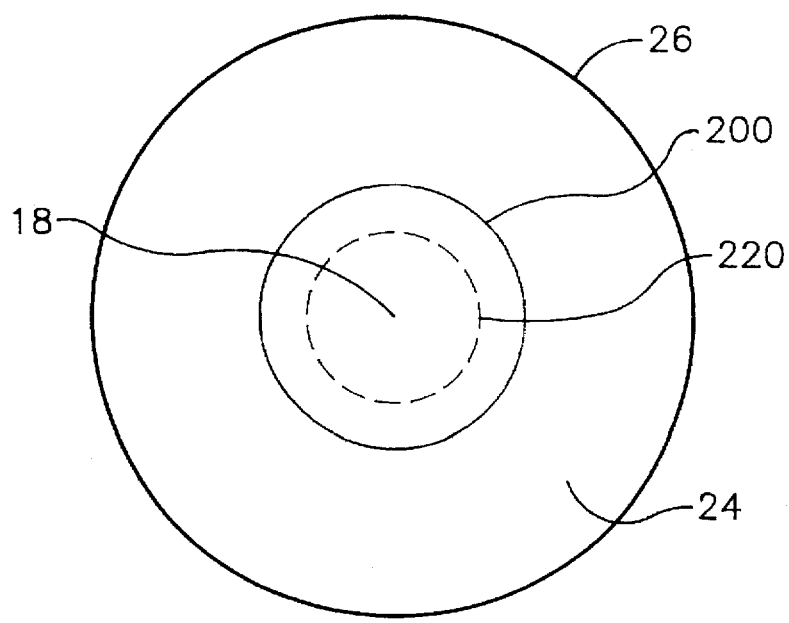
FIG. 4 is a schematic view of an eye's image for showing the position of the overlaid images in the present invention when the eye's pupil is dilated.

To explain the method of the present invention, additional reference will be made to FIGS. 3 and 4 where FIG. 3 is an image view of the eye with its pupil undilated and FIG. 4 is an image view of the eye after pupil dilation, i.e., when the undilated pupil is no longer available. Note that in FIGS. 3 and 4, natural pupil 20 is shown in dashed-line form. This is because natural pupil 20 would not appear in the image views shown in FIGS. 3 and 4. Instead, the image view would "see" entrance pupil 22 which is accordingly shown in solid-line form.

Prior to dilation, eye 10 is imaged by system 100. In general, joystick 108 and image generator 106 cooperate to overlay an image on the image of eye 10 on display 104. The overlaid image is typically a geometric shape sized and positioned to coincide with an anatomical landmark appearing in the image of eye 10. The selected anatomical landmark should be one that remains unchanged in size, shape and position after pupil dilation. For example, one suitable anatomical landmark is limbus 26 which is circular. Accordingly, as a first step in the process, joystick 108/image generator 106 can be operated to position an image of a circle on the image of limbus 26. Next, an image of another circle is positioned at the perimeter of entrance pupil 22. Image coordinates (e.g., centers and radius) associated with the circles overlaid on the image of limbus 26 and on entrance pupil 22 are then stored by image generator 106 for recall in the next phase of the method. The generation of these image coordinates is well-understood in the fields of computer graphics and computer aided design and will therefore not be discussed further herein.

After the above procedure is complete, the eye's pupil can be dilated by one of a variety of techniques known in the art. The image view of eye 10 after dilation is shown in FIG. 4 where the subscript "D" will be added to those elements of eye 10 affected by dilation. Since natural pupil $20_D$ does not typically dilate symmetrically, entrance pupil $20_D$ appearing in the image of eye 10 will also appear asymmetric, i.e., not circular. (Note that the amount of asymmetry is exaggerated in FIG. 4 for purpose of illustration.) Thus, the center of entrance pupil $22_D$ will be shifted relative to the center of entrance pupil 22 determined prior to dilation. Recall that the center of entrance pupil 22 (i.e., prior to dilation) is optical axis 18 in FIG. 3. Further, the optical center or axis 18 of eye 10 is the same both before and after dilation. Accordingly, to accurately locate optical axis 18 after dilation, the image of the circle positioned on limbus 26 prior to dilation is recalled and overlaid on the image of limbus 26 after dilation. Since the center of entrance pupil 22 is known relative to the circle positioned at the image of limbus 22, optical axis 18 is accurately determined after dilation (FIG. 4).

Figure 5:
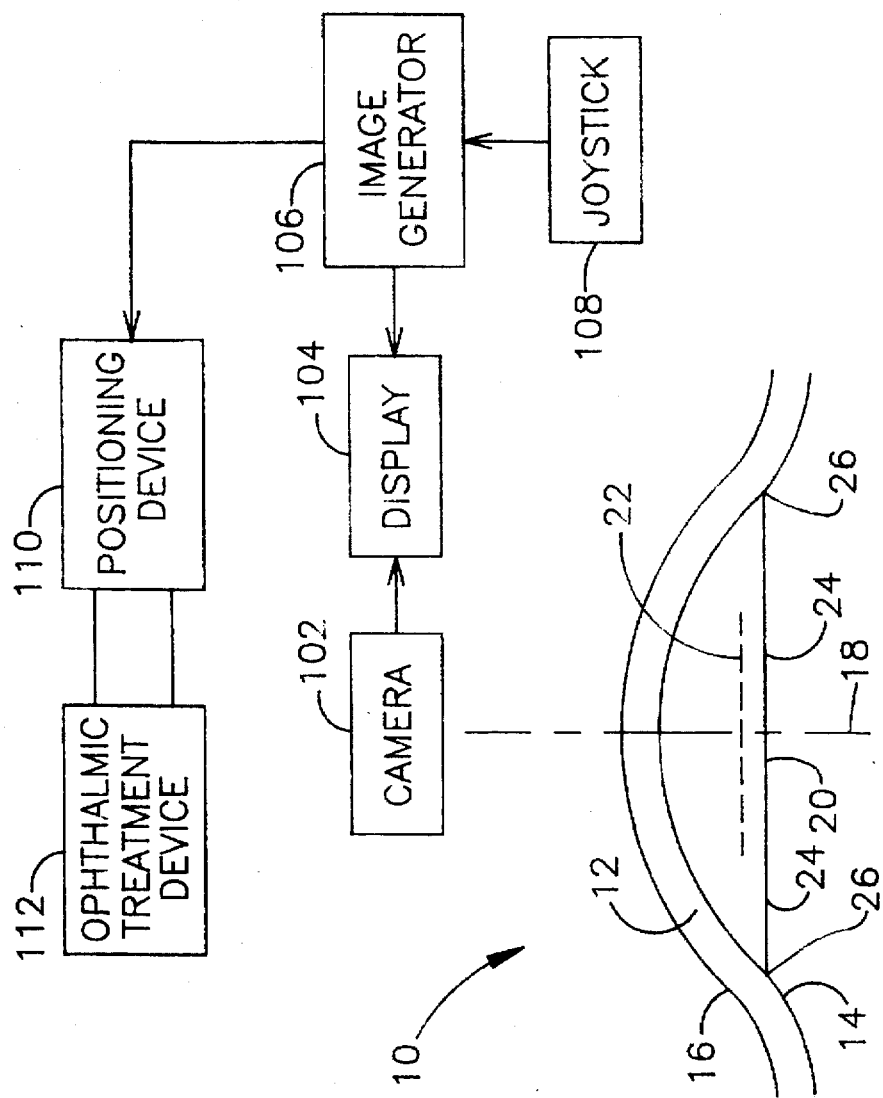
FIG. 5 is a functional block diagram of the system of the present invention coupled to the positioning device of an ophthalmic treatment device.

The advantages of the present invention are numerous. A simple system and method are used to accurately identify the optical axis of an eye after pupil dilation. Since the human eye is very precise in centering rings on top of each other, error produced by the operator is only on the order of a pixel size, e.g., 35 microns. The present invention will find utility both in laboratory research and in clinical application. For example, as shown in FIG. 5, image generator 106 could be coupled to a positioning device 110 used to position an ophthalmic treatment device 112, e.g. an ablation laser. In such an instance, the position of the optical axis properly located after pupil dilation (as descried above) could be used by positioning device 110 to "center" ophthalmic treatment device 112 on the eye's optical axis as a treatment center of reference. For purpose of using the present invention as part of an ophthalmic treatment procedure, the patient should be in the same position or posture during the "before dilation" and "after dilation" phases of the present invention.

Although the invention has been described relative to a specific embodiment thereof, there are numerous variations and modifications that will be readily apparent to those skilled in the art in light of the above teachings. For example, the anatomical landmark presented by the limbus boundary is not the only such landmark that can serve as a reference in the present invention. Other suitable anatomical landmarks include scleral features such as superficial blood vessels, scars, or pigmented deposits.

In addition, although it has been described herein that the eye is imaged before and after dilation from a position on the optical axis of the eye, this may not always be the case. For example, when used in conjunction with an ophthalmic treatment device, the particular equipment setup may require the camera of the present invention to view the eye at an angle relative to the optical axis. The viewing angle to the eye from the camera can introduce error but the level of error is small. One part of the error is caused by viewing the eye off the normal to the plane of the entrance pupil which results in elliptical projection of circles. However, this will not necessarily introduce significant error in the location of the center of the entrance pupil as the circular images can still be fit to the slightly elliptical circles with precision and the resulting recovery of the center of the pupil will still be accurate. The main source of error results from an equipment setup that relies on using the optical center of the natural pupil. As discussed above, the virtual image of the pupil is located 0.55 mm anterior to the natural pupil. (Using the tangent of an off-axis viewing direction, it can be shown that the error in location of the center point at the cornea is about 53 microns per degree of error. If excessive, the error can be compensated for by deliberately shifting the determined optical axis by the discrepancy calculated from the known imaging geometry for viewing angles less than about 30°.) The issue thus becomes how to use the stored data on the location of the center of the natural pupil and it's location relative to the limbus, and how to transfer the location to the front surface of the eye. One way of solving this is as follows.

After dilation, the stored circle for the limbus and the previously measured center of the natural pupil are used to project a circle and cross hair on the image of the eye. The image of the light reflex can be observed in the image and when it is coincident with the cross hair, the line-of-sight of the surgical beam delivery optics is centered over the center of the pupil and normal to the surface of the cornea. If the light reflex is not centered, it will be because the patient's head is titled from a position which places the cornea normal to the line-of-sight. The operator can correct this offset in head tilt manually. Note that it will be a change in tilt, not translation, because of the small field of view of the camera.

It is therefore to be understood that, within the scope of the appended claims, the invention may be practiced other than as specifically described. What is claimed as new and desired to be secured by Letters Patent of the United States is:

1. A method comprising the steps of:
    forming a first image of an eye with its pupil in an undilated state;

referencing the center of said pupil in said undilated state to a reference image of an anatomical landmark of said eye appearing in said first image, wherein image coordinates are used to define the center of said pupil in said undilated state and said reference image;

forming a second image of said eye when said undilated pupil is no longer available for imaging; and positioning said reference image on an image of said anatomical landmark appearing in said second image wherein the center of said pupil in said undilated state referenced to said reference image defines the optical center of said eye.

2. A method according to claim 1 wherein said steps of forming said first image and said second image occur substantially along a line that is normal to said pupil.

3. A method according to claim 1 wherein said step of referencing comprises the steps of:

overlaying a first circular image on said first image;

aligning said first circular image in terms of size and position with an image of the pupil-iris boundary of said eye appearing in said first image, wherein the center of said first circular image so-aligned is the center of said pupil in said undilated state;

overlaying a second circular image on said first image; and aligning said second circular image in terms of size and position with an image of the limbus of said eye appearing in said first image, wherein said second circular image so-aligned is said reference image.

4. A method according to claim 1 further comprising the step of treating said eye using the center of said pupil in said undilated state referenced to said reference image.

5. A method according to claim 4 wherein said step of treating comprises the step of ablating corneal material from said eye.

6. A method of locating the optical center of an eye for corneal treatment thereof, comprising the steps of:

positioning a patient in a posture for receiving said corneal treatment;

forming a first image of an eye of said patient that is to receive said corneal treatment with a pupil of said eye being maintained in an undilated state;

referencing the center of an image of said pupil in said undilated state to a reference circle defined by an image of the limbus of said eye appearing in said first image, wherein image coordinates are used to define the center of said pupil in said undilated state and said reference circle;

dilating said eye to a dilated state;

positioning said patient in said posture for receiving said corneal treatment;

forming a second image of said eye when said pupil is in said dilated state; and positioning said reference circle on an image of the limbus of said eye appearing in said second image wherein the center of said pupil in said undilated state referenced to said reference circle defines the optical center of said eye when said pupil is in said dilated state.

7. A method according to claim 6 further comprising the step of proceeding with said corneal treatment using the center of said pupil in said undilated state referenced to said reference circle.

8. A method according to claim 7 wherein said step of proceeding comprises the step of ablating corneal material from said eye.

9. A method according to claim 6 wherein said step of forming said first image occurs substantially along a line that is normal to said pupil.

10. A method according to claim 6 wherein said step of forming said second image occurs substantially along a line that is normal to said pupil.

11. A method according to claim 6 wherein said steps of forming said first image and said second image occur substantially along a line that is normal to said pupil.

12. A method according to claim 6 wherein said step of referencing comprises the steps of:

overlaying a first circular image on said first image;

aligning said first circular image in terms of size and position with an image of the pupil-iris boundary of said eye appearing in said first image, wherein the center of said first circular image so-aligned is the center of said pupil in said undilated state;

overlaying a second circular image on said first image; and aligning said second circular image in terms of size and position with an image of the limbus of said eye appearing in said first image, wherein said second circular image so-aligned is said reference circle.

13. A system comprising:

a device for forming a first image of an eye with its pupil in an undilated state and for forming a second image of said eye when said undilated pupil is no longer available;

a display coupled to said device for displaying one of said first image and said second image;

an analyzer coupled to said display for locating a center of said undilated pupil in said first image and for locating a position of at least one anatomical landmark in relation to said center of said undilated pupil; and a controller coupled to said analyzer and said display for subsequently aligning said eye based on said position of said at least one anatomical landmark such that said center of said undilated pupil in said eye is properly located.

* * * * *